US009005951B2

(12) United States Patent
Abraham-Fuchs

(10) Patent No.: US 9,005,951 B2
(45) Date of Patent: Apr. 14, 2015

(54) METHOD AND BIOCHIP FOR STUDYING A CHEMICAL SAMPLE

(75) Inventor: Klaus Abraham-Fuchs, Erlangen (DE)

(73) Assignee: Boehringer Ingelheim Vetmedica GmbH, Ingelheim am Rhein (DE)

( * ) Notice: Subject to any disclaimer, the term of this patent is extended or adjusted under 35 U.S.C. 154(b) by 1835 days.

(21) Appl. No.: 11/637,027

(22) Filed: Dec. 12, 2006

(65) Prior Publication Data

US 2007/0141553 A1 Jun. 21, 2007

(30) Foreign Application Priority Data

Dec. 13, 2005 (DE) ......................... 10 2005 059 536

(51) Int. Cl.

| | |
|---|---|
| ***C12N 1/00*** | (2006.01) |
| ***C12Q 1/00*** | (2006.01) |
| ***C12M 1/00*** | (2006.01) |
| ***B01L 3/00*** | (2006.01) |

(52) U.S. Cl.

CPC ........... *B01L 3/5027* (2013.01); *B01L 2200/10* (2013.01); *B01L 2200/143* (2013.01); *B01L 2300/0636* (2013.01)

(58) Field of Classification Search

None

See application file for complete search history.

(56) References Cited

U.S. PATENT DOCUMENTS

| | | | | |
|---|---|---|---|---|
| 6,365,050 | B1 * | 4/2002 | Cauchon | 210/635 |
| 6,403,367 | B1 | 6/2002 | Cheng et al. | |
| 6,440,725 | B1 * | 8/2002 | Pourahmadi et al. | 435/288.5 |
| 6,632,655 | B1 | 10/2003 | Mehta et al. | |
| 7,236,888 | B2 | 6/2007 | Allbritton et al. | |
| 2002/0090320 | A1 * | 7/2002 | Burow et al. | 422/64 |
| 2002/0128801 | A1 * | 9/2002 | Okuno et al. | 702/187 |
| 2004/0038426 | A1 | 2/2004 | Manalis | |
| 2004/0129678 | A1 | 7/2004 | Crowley et al. | |
| 2005/0130292 | A1 | 6/2005 | Ahn et al. | |
| 2005/0208539 | A1 * | 9/2005 | Vann et al. | 435/6 |
| 2005/0233440 | A1 * | 10/2005 | Scurati et al. | 435/287.2 |
| 2005/0252773 | A1 * | 11/2005 | McBride et al. | 204/450 |

FOREIGN PATENT DOCUMENTS

| | | | |
|---|---|---|---|
| WO | WO-00/37163 | | 6/2000 |
| WO | WO-00/50172 | | 8/2000 |
| WO | WO-02/42732 | A2 | 5/2002 |
| WO | WO-03/080866 | A1 | 10/2003 |
| WO | WO-2005/070533 | A1 | 8/2005 |

* cited by examiner

*Primary Examiner* — Robert T Crow

(74) *Attorney, Agent, or Firm* — Roberts Mlotkowski Safran & Cole, P.C.; David S. Safran

(57) ABSTRACT

A method for studying a biological sample in a biochip ("lab-on-a-chip") is disclosed. In at least one embodiment of the method, a biological sample is introduced into the biochip, the sample is subjected to at least one preparation step and, at the end of a measurement cycle, the concentration of a particular analyte is measured. The concentration of a marker substance, which for example is a reaction substance involved in a preparation step, is furthermore measured. A corresponding biochip is further disclosed.

9 Claims, 2 Drawing Sheets

METHOD AND BIOCHIP FOR STUDYING A CHEMICAL SAMPLE

PRIORITY STATEMENT

The present application hereby claims priority under 35 U.S.C. §119 on German patent application number DE 10 2005 059 536.7 filed Dec. 13, 2005, the entire contents of which is hereby incorporated herein by reference.

FIELD

Embodiments of the invention generally relate to a method for studying a biological sample in a biochip, and/or to a biochip suitable for carrying out this method.

BACKGROUND

Biochips measure the concentration or the presence of biomolecules (for example DNA, proteins) in biological samples. A particularly innovative type of biochip is configured so that from the introduction of the sample to the measurement results, all steps for sample preparation and detection are carried out inside a closed unit of the biochip. Such biochips are also referred to as "lab-on-a-chip".

The measurement processes in such a "lab-on-a-chip" may be very complex and comprise a multiplicity of sample preparation steps which precede the actual detection of the intended analyte, for example separation, enrichment, filtering, cell lysis or PCR. These may involve both mechanical and biochemical preparation steps.

Reaction substances which are needed in the course of the sample preparation or the detection either are supplied to the microfluidic system of the biochip from storage containers in the external reader, or they are prepackaged ready for use in storage chambers of the biochip, so-called reservoirs. In order to improve the durability and storability of the biochip, particularly biochemical reaction substances such as proteins and enzymes are often stored in dried form.

In the past, generally only the concentration of the intended analyte is measured in the sensor part of the biochip. If this measurement is faulty, no further measured quantity is available which could provide information about the cause of the measurement error, or which would even permit correction of the measurement error.

SUMMARY

In at least one embodiment of the invention, a method is provided for studying a biological sample in a biochip, as well as a corresponding biochip, with which quality control of the measurement of the intended analyte is possible.

According to at least one embodiment of the invention, a biological sample is introduced into the biochip, the sample is subjected to at least one preparation step and, at the end of a measurement cycle, the concentration or the presence of a particular analyte in the prepared sample is measured, the concentration or the presence of a marker substance furthermore being measured.

The term "measurement cycle" is intended to mean the process taking place on the biochip, which may for example comprise one or more sample preparation steps. A preparation step may be any mechanical or chemical process, in particular one of the aforementioned biochemical reaction steps. The analyte may be any intended substance, in particular biomolecules such as DNA, RNA or proteins.

At least one embodiment of the invention is distinguished in that in addition to determining the concentration or the presence of the intended analyte, a marker substance is also detected. The marker substance is particularly preferably a reaction substance involved in a preparation step. The measurement of the marker substance serves as a quality parameter, and is therefore used either to identify a measurement result as erroneous or even to be able to correct measurement errors which there may be.

In the biochip according to at least one embodiment of the invention, besides the sensor for measuring the intended analyte, at least one further sensor is provided for measuring the concentration or the presence of a marker substance. So-called array technology is particularly preferably used for this, in which a sensor array that makes it possible to measure a multiplicity of different substances simultaneously, without significant extra costs, is integrated into a biochip.

The concentration or the presence of the marker substance is particularly preferably measured not, or not only, at the end of the measurement cycle but after a particular step during the measurement cycle, i.e. as an "intermediate result". This has the advantage that the results of the measurement of the marker substance can be used for controlling the further measurement cycle.

In one example embodiment of the method and biochip, the reaction substances for a sample preparation step, for example cell lysis, are stored as dry reagents covered with a protective membrane in a reservoir in the biochip. The reaction substances may, for example, be enzymes. For a successful measurement, it is necessary that these enzymes are deposited at a sufficient concentration in the biochip, the activity of the enzyme has not been restricted by the storage time and storage conditions, that the protective membrane over the reservoir is disintegrated sufficiently and, lastly, that a sufficient amount of the enzyme is brought in contact with the sample. These facts can be confirmed by measuring the concentration of the enzyme present in the microfluidic circuit of the biochip either at the end of the entire measurement cycle or after a particular step in the measurement cycle, in parallel with the determination of the concentration of the analytes. If the concentration of the enzyme determined in this way lies below a particular threshold, then the measurement of the analyte is identified as erroneous.

It may happen that an insufficient concentration of a reaction substance vitiates the measurement value for the intended analyte in a known way. With an insufficient concentration of the reaction substance below a predetermined threshold, for example, the measurement value may decrease linearly with the concentration of the reagent. In a further embodiment of the invention, the measurement result of the analyte can be corrected in such a case from the measured concentration of a marker substance, which is either the reaction substance itself or is added to it.

In a further embodiment, the protective layer over a reaction substance reservoir may be configured so that breakdown products of the protective layer can be detected in the microfluidic system, when the protective layer has been disintegrated properly. The biochip may then be configured so that one of the detection sensors of the biochip measures the concentration or the presence of breakdown products (for example proteins) of the protective layer in the detection chamber. This information can be used for quality control of the measurement cycle, since it can be inferred from this information that a particular protective layer has been disintegrated and, via the time of the detection, it is also possible to infer the time of the disintegration.

In a further embodiment of the invention, the further measurement cycle in the biochip may also be controlled with the aid of the information measured about a reaction substance concentration at a particular time in the measurement cycle. For example, a subsequent step in the measurement cycle may be triggered in a chronologically defined order by the measured information "protective layer X disintegrated". For example, amplification of DNA material in the sample by a polymerase chain reaction (PCR) may not be started until after a predetermined time interval following the disintegration of a particular protective layer, in order to ensure that a particular step of the sample preparation, for example cell breakup, has had sufficient time to take place completely. In this example embodiment, provision may also be made to use different protective layer materials for different reservoirs in the same biochip so that, for each reservoir, its release can be measured separately and specifically.

A similar type of functionality for determining the time of the release of a reservoir can also be achieved by adding to the reservoir content a marker molecule (for example a protein), the release of which can then be measured by a detection sensor.

The use of a marker added to a reaction substance can generally be used as a substitute for determining the concentration of the reaction substance, when the sensor array existing in the biochip is not suitable for direct measurement of the reaction substance. Then, instead, a marker substance readily detectable by the existing sensors may be added.

In a further embodiment, the marker substances to be determined are coupled to chemical labels, in order to make the measurement simpler or more accurate.

BRIEF DESCRIPTION OF THE DRAWINGS

The invention will now be described in more detail with the aid of an example embodiment with reference to the appended drawings. In the drawings.

DETAILED DESCRIPTION OF THE EXAMPLE EMBODIMENTS

Figure 1:
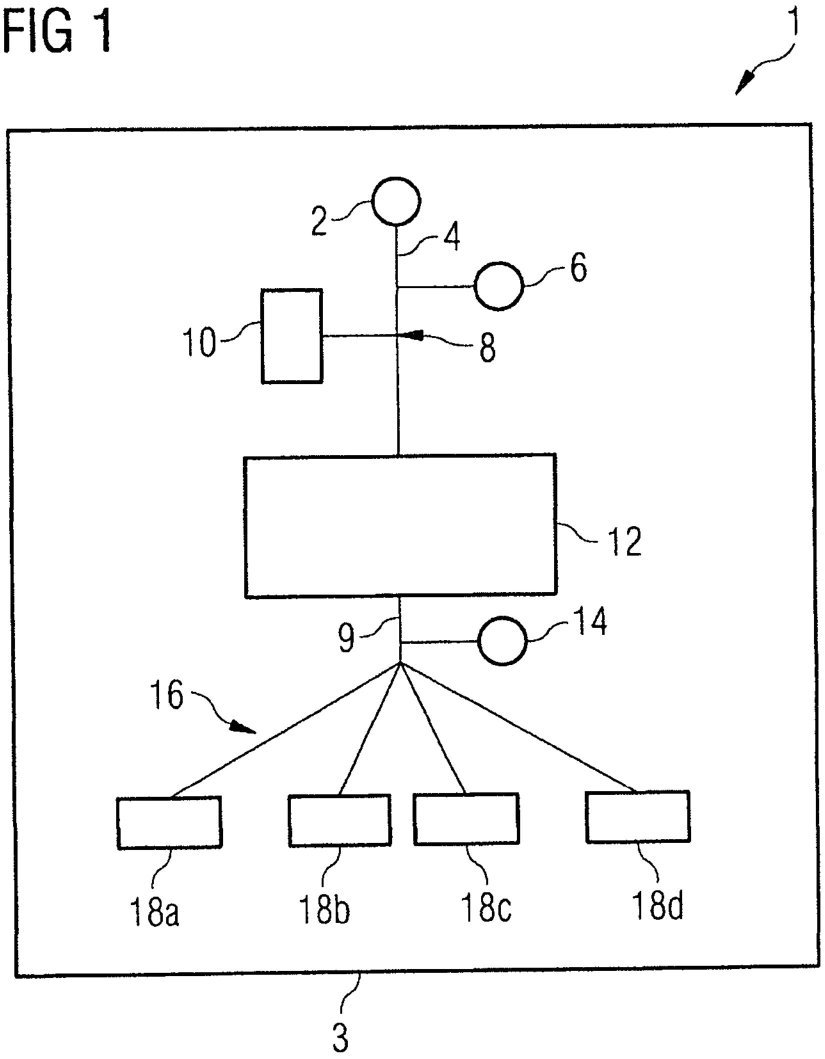
FIG. 1 shows a schematic plan view of a biochip according to one embodiment of the invention.

The terminology used herein is for the purpose of describing particular embodiments only and is not intended to be limiting of the present invention. As used herein, the singular forms "a", "an" and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Referencing the drawings, wherein like reference numerals designate identical or corresponding parts throughout the several views, example embodiments of the present patent application are hereafter described.

Figure 2:
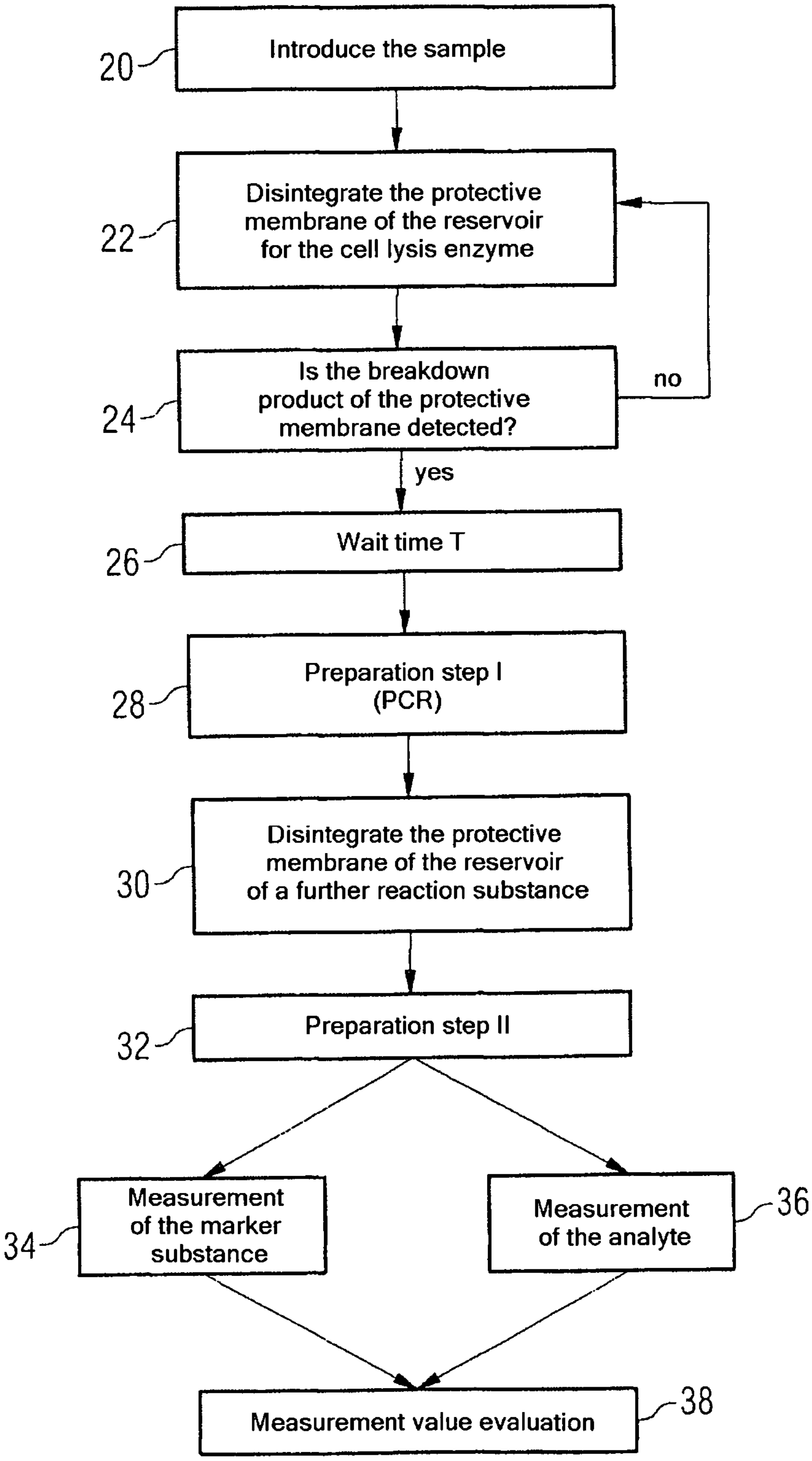
FIG. 2 shows a flow chart of an example embodiment of the method according to the invention.

FIGS. 1 and 2 respectively show one of many conceivable embodiments of the method or biochip according to the invention. For the person skilled in the art, it is clear that marker substances could be measured at further or other points in the measurement cycle and used in miscellaneous ways for controlling the measurement cycle, as well as for quality control.

The biochip 1 schematically represented in FIG. 1 comprises a support 3, which contains a system of microfluidic channels 4. The sample is introduced at the input 2 and delivered through the microfluidic channel 4. The reservoir 6 contains a reaction substance which, for example, is needed for the cell lysis. The reservoir 6 is covered by a protective layer (not shown) which is disintegrated in a known way when initiating the measurement cycle, for example by shining in light. The reaction substance contained in the reservoir 6 thus becomes mixed with the sample 2 in the channel 4, where it leads to the cell lysis.

According to one example embodiment of the invention, a first sensor 10 which measures the concentration of a marker substance is already attached to the branch point 8. This substance may either be the actual enzyme contained in the reservoir 6 or a special marker substance present in the reservoir, or else a breakdown product of the disintegrated protective layer. The sensor 10 can in any case already detect early in the measurement cycle whether the content of the reservoir 6 has been properly brought in contact with the sample. Depending on the result of this measurement, either the measurement cycle may be terminated, the disintegration of the protective layer repeated, or a measurement value measured later may be corrected.

The sample treated in this way is delivered into the device 12 in which a further sample preparation step takes place, for example a polymerase chain reaction (PCR).

After having passed through the PCR device 12, the sample is delivered into the channel 9. Optionally, the content of a further reservoir 14 may be added to the sample. The sample is thereupon divided between a plurality of sensors 18*a*, 18*b*, 18*c* and 18*d* in the multiplexer 16. In this sensor array, for example, sensor 18*a* measures the concentration of the actual analyte while sensors 18*b* to 18*c* detect further marker substances. Optionally, here again it is possible to establish whether the content of the reservoir 14 has properly come in contact with the sample.

The configuration of the sensors 10, 18*a*-18*d* is known per se. They comprise, in particular, a capture molecule which is immobilized on a measurement probe and which binds specifically to the intended analyte or the marker substance. For example, antibodies may be used as capture molecules. Integrated into the capture molecule, there is a reporter molecule which detects the binding and emits an externally measurable electrical, optical or magnetic signal. This can be measured and thus provides information about the presence or the concentration of the analyte or the marker substance. The sensors 10 and 18*a*-18*d* are electrically connected to an evaluation unit (not shown) which processes the measurement results.

An example of the method according to an embodiment of the invention is represented in FIG. 2. Accordingly, the introduction of the sample in step 20 is followed by disintegration of the protective membrane of a reservoir 6 for a cell lysis enzyme in step 22. The concentration of the breakdown product of the protective membrane is measured in the next step 24, for example by the sensor 10. If the concentration lies below a predetermined limit value, then the protective membrane has not been disintegrated sufficiently. This information can now be used for controlling the measurement cycle, in that the mechanism for disintegrating the cell membrane is again reactivated. If the breakdown product of the protective membrane is detected at a sufficiently high concentration, then a predefined time interval T may be waited in step 26 in order to ensure that the cell lysis has had sufficient time to take place completely. The first preparation step 28, for example a PCR, is then carried out.

The protective membrane of the reservoir of a further reaction substance is optionally disintegrated in a subsequent step 30. This may likewise optionally be followed by a second preparation step 32. Lastly, the presence or the concentration of the analyte is measured in step 36. In parallel with this, a further marker substance, which for example was added to the reservoir disintegrated in step 30, may also be measured in step 34. The measurement values of the steps 34 and 36 are lastly evaluated in step 38 in the aforementioned evaluation device. In step 38, for example, a correction of the measurement value of the analyte may be carried out.

The measurement according to an embodiment of the invention, in particular of reaction substances involved in the measurement cycle, allows a novel, quantified form of quality control, error source analysis, measurement value correction or else improved control of the measurement cycle in a biochip.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for studying a biological sample in a biochip having a closed unit configuration with a system of microfluidic channels, a sample input and a reservoir that contains a reaction substance that is covered by a disintegrateable protective layer, comprising:

introducing a biological sample into the biochip;

causing the protective layer to disintegrate so as to result in the reaction substance contained in the reservoir becoming mixed with the sample, subjecting the biological sample to at least one preparation step in which the reaction substance is involved;

measuring, at the end of a measurement cycle, at least one of a concentration and a presence of a particular analyte in the prepared biological sample; and measuring at least one of a concentration and a presence of a marker substance, wherein the marker substance is a breakdown product of the protective membrane, wherein the measurement of the at least one of the concentration and the presence of the marker substance is used for at least one of controlling the measurement cycle and quality control wherein, prior to said preparation and measuring steps, a first sensor measures the concentration of a marker substance to detect whether the content of the reservoir has been properly brought into contact with the sample, and depending on the concentration of the marker substance detected, the measurement cycle may be terminated, the step of causing the protective layer to disintegrate repeated, or results of said measuring steps subsequently corrected.

2. The method as claimed in claim 1, wherein the marker substance is the reaction substance involved in the preparation step.

3. The method as claimed in claim 1, wherein the marker substance is stored in a dried form on the biochip before the measurement cycle.

4. The method as claimed in claim 1, wherein the marker substance is an enzyme which is involved in the preparation step, and which is used for cell lysis.

5. The method as claimed in claim 1, wherein a plurality of different protective membranes are on the biochip and the plurality of different protective membranes consist of different chemical compositions in order that disintegration of the plurality of different protective membranes is detected individually.

6. The method as claimed in claim 1, wherein the at least one of the concentration and the presence of the marker substance is measured after a particular step during the measurement cycle.

7. The method as claimed in claim 1, wherein the at least one of the concentration and the presence of the marker substance is measured several times during the measurement cycle.

8. The method as claimed in claim 2, wherein the marker substance is stored in a dried form on the biochip before the measurement cycle.

9. The method as claimed in claim 1, wherein the marker substance is a protein.

* * * * *